United States Patent [19]
Troost et al.

[11] Patent Number: 5,611,844
[45] Date of Patent: Mar. 18, 1997

[54] METHOD FOR SAMPLING AND ANALYZING LANDFILL GAS

[75] Inventors: John Troost, Lafayette, La.; George Prokuda, Mukwonago; James A. Petersen, Waukesha, both of Wis.

[73] Assignee: Dresser Industries, Inc., Dallas, Tex.

[21] Appl. No.: 399,069

[22] Filed: Mar. 8, 1995

(Under 37 CFR 1.47)

[51] Int. Cl.$^6$ .......................... B01D 15/08; B01D 53/14
[52] U.S. Cl. .......................... 95/82; 73/23.37; 73/23.41; 95/237
[58] Field of Search ................... 73/23.31, 23.35, 73/23.37, 23.41, 52; 95/82–89, 237–240

[56] References Cited

U.S. PATENT DOCUMENTS

| | | | |
|---|---|---|---|
| 1,965,100 | 7/1934 | Groll et al. | 95/238 X |
| 4,314,027 | 2/1982 | Stahr | 95/82 X |
| 5,071,454 | 12/1991 | Streitberger et al. | 95/237 |
| 5,358,557 | 10/1994 | Jiang et al. | 95/82 |
| 5,512,084 | 4/1996 | Mauterer | 95/237 X |
| 5,529,612 | 6/1996 | Troost | 95/237 X |

FOREIGN PATENT DOCUMENTS 1142146  2/1985  U.S.S.R. .................. 95/239

*Primary Examiner*—Robert Spitzer
*Attorney, Agent, or Firm*—Andrus, Sceales, Starke & Sawall

[57] ABSTRACT

A method for sampling and analyzing landfill gas, in which the landfill gas, which consists primarily of methane and contains volatile organic components, is passed through a quantity of liquid tetraglyme to cause the volatile organic components to be absorbed in the tetraglyme. The tetraglyme containing the absorbed volatile organic components, is then disposed in a sealed container with zero headspace and transported to a laboratory testing facility. At the testing facility, at least a portion of the tetraglyme is withdrawn from the container, dispersed in water, and subjected to a gas chromatography/mass spectrometry procedure to analyze the volatile organic components.

10 Claims, 1 Drawing Sheet

METHOD FOR SAMPLING AND ANALYZING LANDFILL GAS

BACKGROUND OF THE INVENTION

Through decomposition of waste in landfills, gas is generated, which consists primarily of methane, along with volatile organic compounds. The volatile organic compounds can consist of hydrocarbons, which are relatively inert, or can be halogen compounds containing chlorine, bromine, fluorine, or iodine, which are reactive. In addition, the volatile organic compounds may include aromatic hydrocarbons, such as benzene, toluene, xylene, and the like, which are classified as carcinogenic. The type and concentration of the volatile organic compounds can vary from site-to-site, depending upon the nature of the waste in the landfill.

It has been the practice, in the past, to vent the gas from the landfill. In a typical installation, a number of perforated wells or pipes are distributed throughout the landfill to collect the gas, and the gas is then conducted to a manifold or header for discharge from the landfill. As the landfill gas consists primarily of methane, it has been proposed to use the landfill gas as a fuel for gas aspirated internal combustion engines. The engines can be used at the landfill site for generating electricity or steam, pumping, or other functions. At a typical landfill there may be from two to six engines that are operating on the landfill gas.

The presence of certain volatile organic compounds in the landfill gas, particularly the halogenated compounds, can cause serious problems with operation of the engine. Due to the reactivity of these compounds they can react with other constituents to form acids which can attack or corrode engine bearings, bushings, valve guides and stems, as well as producing deposits on the valve seats, and deterioration of the engine oil.

Because of these potential problems with the use of landfill gas, it is important to determine the type and concentration of the volatile organic compounds in the landfill gas. If it is found that the landfill gas has a high concentration of volatile organic compounds that could have a deleterious effect on engine operation, steps can be taken to reduce the concentration of the volatile organic compounds by flaring-off the gas for an extended period, or alternately, treating the gas by catalytic processes to remove or reduce the volatile organic compounds to acceptable limits.

In order to sample and analyze the landfill gas prior to using the gas as a fuel for an internal combustion engine, several methods have been employed. It has been proposed to collect the landfill gas in plastic or metal containers, and then ship the containers to a laboratory for analysis, using a standard gas chromatography/mass spectrometry (GC/MS) procedure. However, it has been found that the volatile organic compounds tend to "plate out" on the plastic or metal containers, with the result that the analysis is flawed and results in a lesser and inaccurate determination of the concentration of the volatile organic compounds.

It has also been proposed in the past to sample and analyze the landfill gas by a tenax tube method. In this method, a quantity of granular aluminum oxide is contained within a small tube, approximately four inches long, and the landfill gas is fed through the tube, and the volatile organic compounds will be absorbed on the granular material. The tube is then sealed and shipped or transported to a laboratory for analysis. To analyze the material, the tube is uncapped and the granular material is heated through induction heating to vaporize the absorbed contaminants, which are then subjected to the standard GC/MS analysis.

The tenax tube sampling method has several disadvantages. First, the sampling method has a relatively short shelf life, in that the volatile organic compounds tend to migrate or desorb from the granular aluminum oxide carrier, so that when the shipping container is opened, the volatilized compounds will escape, so that the resulting analysis is flawed.

Secondly, the tenax tube sampling system is a "one shot" procedure, in which all of the gas released from the granular material on the induction heating is used for a single analysis in the GC/MS procedure. There is no capability of using only a portion of the volatilized gas in order to run additional tests to verify the results.

Further, the tenax tube sampling system also requires that the laboratory have thermal desorption equipment in order to vaporize and release the volatile organic compounds from the tenax material. It has been found that not all analysis laboratories have such equipment.

Therefore, there has been a distinct need for a simple and effective method of accurately sampling and analyzing landfill gas that could be repeated by different laboratories using standard sampling and analytical techniques.

SUMMARY OF THE INVENTION

The invention is directed to a method of sampling and analyzing a gas containing volatile organic compounds and particularly to a method of sampling and analyzing landfill gas. In accordance with the invention, a given volume of landfill gas is passed serially through one or more impingers, each containing a quantity of liquid tetraglyme. The gas is bubbled up through the tetraglyme and the volatile organic compounds are absorbed in the tetraglyme.

To increase the efficiency of the absorption, it is preferred to chill the tetraglyme to a temperature below 0° C. and preferably in the range of about 0° C. to −30° C. The low temperature will minimize volatilization of certain volatile organic compounds that have low boiling points. After the given volume of gas has passed through the tetraglyme, the tetraglyme is transferred to a sealed container, with the tetraglyme substantially filling the entire volume, so that there is minimum headspace in the container. With minimum headspace, the low boiling point organic compounds will not volatilize and will be retained in the absorbed condition in the tetraglyme.

At the site of analysis, at least a portion of the tetraglyme is withdrawn from the sealed container, mixed with water, and subjected to a standard gas chromatography/mass spectrometry instrumentation to obtain an analysis of the volatile organic compounds. With the invention, detection limits of 1 mg/m$^3$ for organic compounds can be achieved when sampling a volume of landfill gas in the order of six liters.

The tetraglyme has a powerful affinity for organic compounds and will act to trap and retain the targeted volatile organic compounds with simplicity and low cost. With the method of the invention, the analysis can be made by any laboratory having the GC/MS instrumentation.

Since refrigerated tetraglyme has been shown to retain the trapped volatile compounds for extended periods of time, the analysis may be carried out long after the sampling without adversely effecting the integrity of the analysis.

In addition, only a portion of the tetraglyme need be analyzed at any one time and this enables additional portions to be subsequently analyzed to verify the original results.

Other objects and advantages will appear in the course of the following description.

DESCRIPTION OF THE DRAWINGS

The drawings illustrate the best mode present contemplated of carrying out the invention.

In the drawings.

DESCRIPTION OF THE ILLUSTRATED EMBODIMENT

Figure 1:
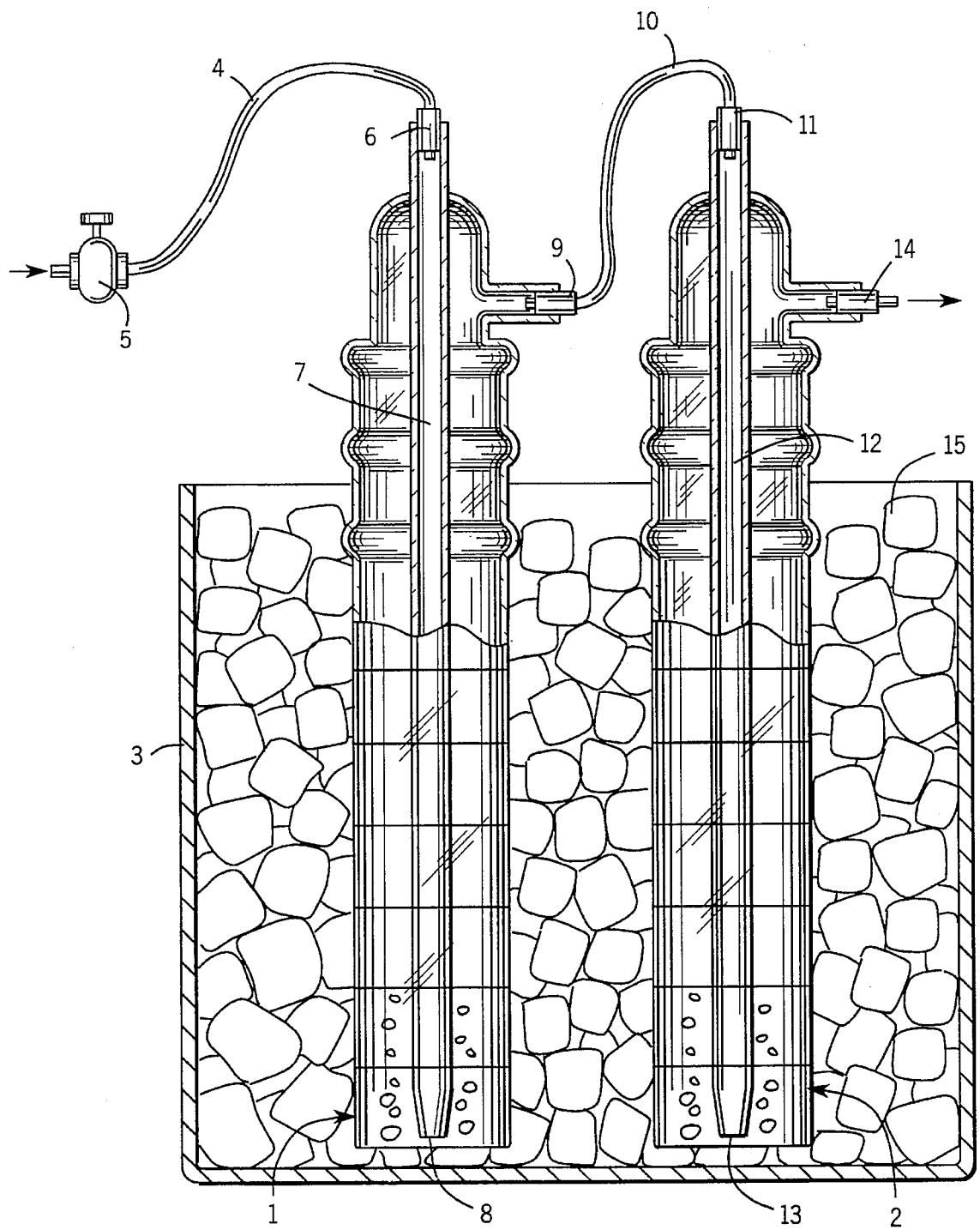
FIG. 1 is a diagrammatic view of the sampling device.

Landfill gas has been increasingly popular recently as a fuel, although the complicated nature of the composition of the landfill gas has not permitted the industry to define precise standards for sampling, analyzing or using the gas as a fuel. Landfill gas consists primarily of methane, along with various volatile organic compounds and, in some cases, volatilized inorganic compounds. A typical landfill gas may contain halogenated volatile organic compounds, such as chlorobenzene, dichlorobenzene, dichlorethane, dichloroethene, chloromethane, methylene chloride, tetrachloroethane, trichloroethane, trichloroethene, vinyl chloride, and the like. In addition, the landfill gas may also include aromatic hydrocarbons, such as benzene, styrene, toluene, xylene, and the like. Siloxane compounds, such as octamethyl cyclotetrasiloxane and decamethyl cyclopentasiloxane may also be present.

The halogenated volatile organic compounds are particularly troublesome when using the landfill gas as a fuel for an internal combustion engine. These compounds are reactive and can react with other constituents in the gas to form acids, which can corrode the bearings, bushings, and valve guides and stems of the engine. In addition, the halogenated organic compounds can also produce deposits on the valve seats, and can deteriorate the engine oil. Because of this, it is desirable to sample and analyze the landfill gas prior to using the gas as a fuel for the engine, as well as sampling and analyzing the gas periodically during operation of the engine.

In accordance with the invention, a novel sampling and analyzing method is provided in order to determine the type and concentration of various volatile compounds in the gas which could have a deleterious effect on engine operation.

In a typical landfill operation, a number of perforated wells, or pipes, are located in a random pattern throughout the landfill and are used to collect the landfill gas. The wells are connected to a common manifold or header, and the gas is then distributed from the header to one or more engines that are located at the landfill site. In a typical installation, the suction side of a pump is connected to the manifold, and the gas is pumped, under pressure, by the pump to the engine. Before being introduced to the engine, it is also customary to remove moisture from the landfill gas, such as by passing the gas through a chiller.

FIG. 1 shows a sampling device which is used to sample a quantity of gas just prior to the gas being introduced to the engine. The sampling device includes a pair of small impingers 1 and 2, which typically may have a volume of about 50 to 60 ml. Impingers 1 and 2 are mounted in an open-top container or tank 3. An inlet line 4 is connected to the fuel line of the engine, and a valve 5, preferably a needle valve, is mounted in line 4, and serves to control the flow of the landfill gas through line 4 to the impinger 1.

Each impinger 1 and 2 contains a quantity of tetraglyme (tetraethylene glycol dimethyl ester). Tetraglyme is an organic solvent, soluble in water, and has a boiling point of 276° C.

Tetraglyme has a high affinity of polar and non-polar, low and high boiling, halogenated and non-halogenated, aromatic and aliphatic compounds.

As shown in the drawing, line 4 is connected to a fitting 6, which is mounted in the upper end of impinger 1, and a tube 7 is mounted concentrically within the impinger and is provided with an outlet 8 in its lower end. The landfill gas entering the impinger 1 through fitting 6, will flow downwardly through tube 7, and is discharged through outlet 8, bubbling upwardly through the quantity of tetraglyme contained in the impinger 1.

As the landfill gas flows upwardly through the tetraglyme in impinger 1, the volatile, organic compounds will be absorbed in the tetraglyme. The landfill gas is then discharged from the upper end of impinger 1 through an outlet fitting 9, and is conducted through a hose or line 10 the inlet fitting 11 of the second impinger 2. Impinger 2 is constructed in the same manner as impinger 1, and includes a central tube 12, having an outlet 13 in its lower end. The landfill gas flows downwardly through tube 12, and is discharged through outlet 13, flowing upwardly through the tetraglyme contained within the impinger 2, to thereby cause absorption of the volatile compounds in the tetraglyme. The landfill gas is then discharged through outlet fitting 14 in the upper end of impinger 2 to the atmosphere, or other site.

The landfill gas flowing through impinger 1 and 2 is pressurized, and normally is at a pressure in the range of about 2 to 8 psi, and preferably about 120 psi. In practice, about six liters of gas are passed through the impingers 1 and 2, and through operation of the valve 5, the flow rate of the gas is generally in the range of about 50 to 500 ml per minute, and preferably about 100 ml per minute.

It has been found that the retention and detection limits for several of the volatile organic compounds can be improved by maintaining the tetraglyme at a low temperature, preferably below 0° C., and generally in the range of about 0° C. to −30° C. This low temperature can be achieved by locating the impingers 1 and 2 within an ice bath 15 or a salt/ice bath in container 3.

The use of the low temperature will minimize volatilization of certain volatile organic compounds that have low boiling points, such as chloromethane, vinyl chloride and chloroethane. In addition, lowering the temperature of the tetraglyme will increase its viscosity, so that the gas will bubble through the tetraglyme at a slower rate, thus increasing the residence time of the gas within the tetraglyme.

While the drawing shows two impingers being employed, it is contemplated that one or more impingers may be used. The advantage of multiple impingers is that volatile compounds, which may not have been absorbed by the tetraglyme in the first impinger in the series, may be absorbed in the tetraglyme in the second impinger, thus increasing the efficiency of the sampling.

After the desired volume of landfill gas has been passed through the impingers 1 and 2, the tetraglyme is poured from the impingers into a shipping container or tube, and sealed within the tube. The low boiling point organic compounds will not volatilize and will be retained in the tetraglyme. The tetraglyme in the shipping container is then transported at a low temperature, preferably on ice, to a suitable laboratory site for analysis using a standard gas chromatography/mass spectrometry (GC/MS) procedure, as set forth in EPA method 8240. In performing the analysis, a portion of the tetraglyme containing the absorbed volatile organic compounds is removed from the shipping container and dispersed in water, preferably in a ratio of about 100 microliters of tetraglyme per 5 ml of water. This sample is then subjected to standard GC/MS instrumentation to obtain an analysis of the volatile organic compounds.

With the invention, detection limits of 1 mg/m$^3$ of organic compounds can be achieved when sampling six liters of the landfill gas. Even lower detection limits can be achieved by using greater volumes of gas, or by dispersing greater quantities of tetraglyme into water, as for example, using 500 ml of tetraglyme with 25 ml of water for the analysis.

The method of the invention can also detect inorganic contaminants in the gas, but the inorganics must be present in a vaporized form, or be attached to air borne particulates.

The invention provides distinct advantages over prior sampling and analyzing methods for landfill gas. The tetraglyme impingers effectively trap and retain all of the targeted volatile organic compounds with simplicity and low cost. The chilled tetraglyme has a powerful affinity for all pollutants and hazardous substance list volatile organics, including polar, non-polar, high and low boiling, halogenated and non-halogenated, and aromatic and aliphatic materials.

The sampling method of the invention using the tetraglyme has a substantially greater shelf life than prior sampling methods, so that the time period between the sampling and analysis is not as critical.

As a further advantage, only a portion of the tetraglyme need be analyzed at any one time, and this enables additional portions of the tetraglyme to be subsequently analyzed to verify the original results. This differs from prior methods, in which it was necessary to analyze the entire sample, so that there was no remaining portion of the sample that could be subsequently analyzed for verification.

Further, with the method of the invention, the characterization of the volatile organics can be made by routine water analysis GC/MS methodologies, so that the analysis can be performed by any laboratory having ordinary GC/MS instrumentation.

The invention also preserves the sample integrity, in that there is no possibility of the volatile organic compounds plating out on the wall of any container during shipment or handling.

While the above description has shown the invention as used for sampling and analyzing landfill gas, it is contemplated that the invention can also be used in other instances where gas analysis including ambient air is required.

We claim:

1. A method of sampling and analyzing a gas containing volatile organic compounds, comprising the steps of passing the gas through a quantity of liquid tetraglyme to cause the volatile organic compounds to be absorbed in the tetraglyme, mixing said tetraglyme with water to form a dispersion, and thereafter subjecting the dispersion to gas chromatography/mass spectrometry analysis to analyze the volatile organic compounds.

2. The method of claim 1, and including the step of maintaining the tetraglyme at a temperature below 0° C. when the gas is passed through said tetraglyme.

3. The method of claim 1, and including the step of passing a preselected volume of gas through said tetraglyme.

4. The method of claim 1, and including the step of disposing the tetraglyme in an impinger, said step of passing the gas through the tetraglyme comprises flowing the gas upwardly through the tetraglyme in said impinger.

5. The method of claim 1, and including the step of disposing the tetraglyme in a pair of individual impingers, said step of passing the gas through the tetraglyme comprising flowing the gas upwardly through the tetraglyme in a first of said impingers and then flowing the gas upwardly through the tetraglyme in a second of said impingers.

6. A method of sampling and analyzing landfill gas, comprising conducting gas comprising methane and containing volatile organic compounds from a landfill site, passing a preselected volume of said gas through a quantity of liquid tetraglyme to thereby absorb said volatile organic compounds in said tetraglyme, withdrawing at least a portion of the tetraglyme from the container and mixing the tetraglyme with water to form a mixture, and subjecting the mixture to a gas chromatography/mass spectrometry analysis to analyze the composition of said volatile organic compounds.

7. The method of claim 6, and including the step of maintaining the temperature of said tetraglyme at a value in the range of 0° C. to −30° C.

8. The method of claim 6, and including the step of removing water vapor from said gas prior to passing the gas through said tetraglyme.

9. The method of claim 6, wherein said gas is passed through said quantity of tetraglyme at a flow rate of about 50 to 500 ml/minute.

10. A method of sampling and analyzing landfill gas, comprising conducting landfill gas composed of methane and volatile organic compounds from a landfill site, passing a preselected volume of said gas through a quantity of liquid tetraglyme contained within an impinger and flowing the gas upwardly through said quantity of tetraglyme to thereby cause the volatile organic compounds to be absorbed in said tetraglyme, transferring the tetraglyme with the absorbed volatile organic compounds to a container, maintaining the tetraglyme in the container at a temperature of about 0° C., transferring the container to an analysis site, withdrawing at least a portion of the tetraglyme from the container at the analysis site, and subjecting the withdrawn tetraglyme to a gas chromatography/mass spectrometry procedure to analyze the composition of said volatile organic compounds.

* * * * *